United States Patent [19]

Marsh

[11] Patent Number: 4,825,686
[45] Date of Patent: May 2, 1989

[54] VAGINAL DIAPHRAGM TESTING

[76] Inventor: Stephen A. Marsh, 21 Payson Estate, 456 Belmont St., Watertown, Mass. 02172

[21] Appl. No.: 65,262

[22] Filed: Jun. 22, 1987

[51] Int. Cl.⁴ .............................................. G01M 3/26
[52] U.S. Cl. ......................................... 73/40; 206/37; 206/459
[58] Field of Search .............. 73/40; 340/605; 206/37, 206/38, 69, 438, 459, 569

[56] References Cited

U.S. PATENT DOCUMENTS

| | | |
|---|---|---|
| 682,183 | 9/1901 | Etheridge . |
| 1,503,411 | 7/1924 | Zimmerman . |
| 2,074,140 | 3/1937 | Bates ................................. 73/40 X |
| 2,273,489 | 2/1942 | Holmes . |
| 2,567,926 | 9/1951 | Dunkelberger ..................... 73/40 X |
| 3,081,620 | 3/1963 | Glass ................................... 73/40 |
| 3,315,519 | 4/1967 | Ferguson ............................. 73/40 |
| 4,272,959 | 6/1981 | Yamane .......................... 340/605 X |
| 4,289,232 | 9/1981 | Seibel ................................... 206/37 |

Primary Examiner—Stewart J. Levy
Assistant Examiner—Joseph W. Roskos

[57] ABSTRACT

A device and method for testing the integrity of a vaginal diaphragm having an annular ring about a membrane desired to be nonporous consists of a base member defining a surface for engaging the ring in sealing relationship and defines, with the membrane, a pressure chamber, a clamp for clamping the ring in sealing relationship upon the surface, apparatus for creating an inflating pressure condition in the chamber of a level predetermined to cause loss of air from the chamber through the membrane if the membrane has in excess of predetermined maximum degree of porosity, and an indicator of loss of air from within the chamber. Preferably the clamp is defined by a cover, and the device is in the form of a protective carrying case for the diaphragm.

12 Claims, 1 Drawing Sheet

VAGINAL DIAPHRAGM TESTING

BACKGROUND OF THE INVENTION

The invention relates to testing the integrity of a contraceptive device, namely a vaginal diaphragm, for leakage, prior to use.

The vaginal diaphragm is a popular method of contraception, particularly as it is recognized as a safe and effective family planning method without associated chemical side effects. The diaphragm operates by preventing sperm from entering into the uterus and fertilizing an ovum. The vaginal diaphragm has an annular ring which fits about the uterus within the vagina in the region of the portio vaginalis. The diaphragm also includes a dome shaped membrane which blocks the external uterine orifice. In order for the diaphragm to operate effectively, perforations or porosity must not be present in the membrane in excess of a predetermined maximum degree.

The method of testing recommended by one diaphragm manufacturer is to hold the diaphragm up to a light source and visually inspect for perforations, thus relying entirely upon the degree of care and level of ability of the user. However, such an inspection method will not detect small perforations, e.g., of the order of 0.030 inch. Until now, there is no known portable device for reliably testing the integrity of a vaginal diaphragm for small perforations.

SUMMARY OF THE INVENTION

According to the invention, a device for testing the integrity of a vaginal diaphragm having an annular ring about a membrane desired to be nonporous, comprises a base member defining a surface for engaging the ring in sealing relationship and further adapted to define, with the membrane, a pressure chamber, clamping means for clamping the ring in sealing relationship upon the surface, pressurizing means for creating an inflating pressure condition in the chamber of a level predetermined to cause loss of air from the chamber through the membrane if the membrane has in excess of a predetermined maximum degree of porosity, and means for indicating loss of air from within the chamber.

In preferred embodiments, the device further comprises a protective carrying case for the vaginal diaphragm, the base member forming a first element of the case, sized and constructed to receive the vaginal diaphragm, and the case further comprising a cover sized and constructed to be disposed upon the base member. Preferably the cover defines the clamp means, and, more preferably the cover when closed upon the base is constructed and arranged to accommodate expansion of a vaginal diaphragm in response to the pressure condition. Also, more preferably, the cover is hingedly attached to the base member, and the ring, with the cover closed upon the base member, is held by the clamp means defined by the cover in sealing relationship upon the surface defined by the base member. Preferably the pressurizing means comprises a bellows and a one way valve for flow of air into the chamber, and the indicating means comprises an indicating chamber in fluid communication with the pressure chamber, and a pressure responsive element within the indicating chamber. Alternatively, the indicating means could comprise the cover sized and configured to cooperate with the diaphragm to indicate loss of air in the chamber, or a pressure responsive element in the cover.

According to another aspect of the invention, an assembly for transporting and integrity-testing of a vaginal diaphragm comprises a protective carrying case, and, disposed therewithin, a vaginal diaphragm having an annular ring about a membrane desired to be nonporous, the container comprising a base member defining a surface adapted to engage the ring in sealing relationship, the vaginal diaphragm disposed upon the surface, the base member and the membrane together adapted to define a pressure chamber, a cover sized and constructed to be disposed upon the base, with the vaginal diaphragm within the container, the cover defining clamping means for urging the ring into sealing engagement upon the surface, pressurizing means for creating an inflating pressure condition within the chamber of a level predetermined to cause loss of air from the chamber through the membrane if the membrane has in excess of a predetermined maximum degree of porosity, and means for indicating loss of air from within the chamber.

In preferred embodiments of this aspect of the invention, the assembly is in the form of a prepackaged unit suitable for distribution or sale. The cover is constructed and arranged to accommodate expansion of a vaginal diaphragm to the pressure condition within the protective carrying case. The cover is hingedly attached to the base member, and the ring, with the cover closed upon the base member, is held by the clamp means defined by the cover in sealing relationship upon the surface defined by the base member.

According to still another aspect of the invention, a method for testing the integrity of a vaginal diaphragm having an annular ring about a membrane desired to be nonporous comprises providing a base member defining a surface adapted to engage the ring in sealing relationship and further adapted to define, with the membrane, a pressure chamber, placing the ring in sealing engagement upon the surface, creating an inflating pressure condition in the chamber of a level predetermined to cause loss of air from the chamber, through the membrane, if the member has in excess of a predetermined maximum degree of porosity, and, for a predetermined period of time, monitoring the chamber for loss of air.

In a preferred embodiment, the method further comprises clamping the ring onto the surface, and providing a container for the vaginal diaphragm comprising the base member and a cover, and closing the cover to sealingly clamp the ring upon the surface, and monitoring preferably comprises observing the position of a pressure responsive indicating element.

Thus there is provided by the invention a portable device and method for rapidly and reliably testing the integrity of vaginal diaphragms prior to use.

These and other objectives and features of the invention will be understood from the following description of a preferred embodiment, and from the claims.

DESCRIPTION OF THE PREFERRED EMBODIMENT

We first briefly describe the drawings.

Figure 2:
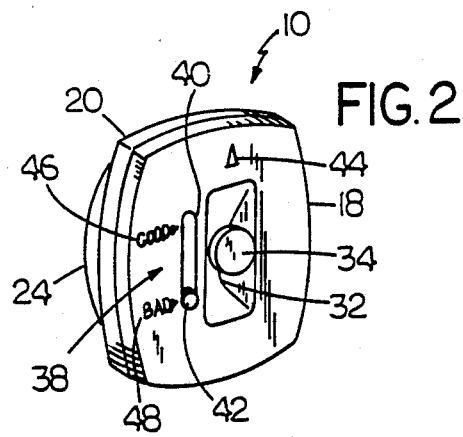
FIG. 2 is a similar view of the device of the invention, showing the base surface of the device.
Figure 1:
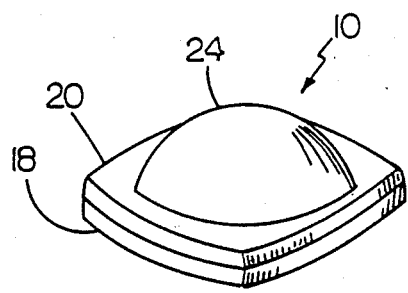
FIG. 1 is a perspective view of the device of the invention containing a contraceptive device, namely a vaginal diaphragm.

Referring to FIGS. 1-5, there is shown a device 10 of the invention, a protective carrying case for transporting and integrity testing a contraceptive device, namely a vaginal diaphragm, for leakage. The vaginal diaphragm 12 consists of an annular ring 14 about a dome shaped membrane 16. The degree of protection afforded to the user by this contraceptive device is, of course, dependant upon an effective absence of porosities in the membrane. The device of the invention permits a consumer to simply and rapidly detect the presence of porosity in excess of a predetermined maximum degree in the diaphragm membrane tested.

The protective carrying case 10 consists of a base member 18 and a hinged cover 20. The base member includes a trough which defines an annular sealing surface 22. The inner and outer diameters of the sealing surface 22 are selected to at least encompass the usual range of outer diameters of annular ring 14 of a vaginal diaphragm so that the diaphragm is received within the trough and the ring 14 rests upon surface 22.

The outer surface of the cover 20 includes a dome 24. The inner surface of the cover 20 includes an inward facing circumferential lip 26 at the base of the dome 24. The circumferential lip 26 defines an annular surface 27 opposed to at least a portion of the surface 22, and, similarly, has inner and outer diameters selected to accommodate the usual range of diameters of vaginal diaphragm rings 14 whereby the surfaces 22, 27 are sized to lie in opposition with a diaphragm ring 14 sealing disposed therebetween.

When the diaphragm 12 is inserted into the device 10, with the annular ring 14 resting on the sealing surface 22, the cover 20 may be closed causing the circumferential lip 26 to clamp down upon the annular ring 14 upon surface 22, the vertical dimension, G, of th gap between the surface 22, 27 predetermined to cause the opposed surfaces to engage upon the ring 14 without engaging upon membrane 16 in a manner that could seal the membrane about the periphery and thus prevent detection of the presence of an unacceptable level of porosity. The clamping force of the lip 26 upon the resilient ring 14 creates a tight seal between the ring and the sealing surface 22. The sealed region within the membrane defines a pressure chamber 28.

Centrally located within the base member 18 is a housing 30 which projects into the pressure chamber 28 and supports a plastic, accordian-like bellows 32. At the outside of the bellows 32 is a button 34 which permits the bellows to be conveniently depressed. The inside of the bellows, within the pressure chamber 28, includes a one way valve 36 which permits air to enter the pressure chamber 28 when the button 34 is depressed, but prevents air from escaping when the button is released.

The base member 18 preferably includes an indicator 38 having a clear elongated chamber 40 and containing an indicator bead 42. The indicator chamber 40 is in fluid communication with the pressure chamber 28. The base member 18 is marked with indicia useful in testing the diaphragm including an arrow 44, and words "GOOD" (46) and "BAD" (48). Both words are located adjacent to the indicator 38, the word "GOOD" being located nearest to the arrow 44, and the word "BAD" being located opposite thereto. The indicator bead 42 is preferably a hollow, plastic, air-tight ball which is filled with air at atmospheric pressure. The indicator bead 42 has a specific weight slightly higher than the specific weight of air at atmospheric pressure. The bead 42 could alternately be fabricated as a solid ball of an expanded material having the appropriate aggregate specific weight. Thus, when the air pressure within the chambers 28 and 40 is at a first level, below a predetermined test pressure, the weight of the indicator bead 42 exceeds the buoyant force exerted upon the bead by the air and the bead is disposed in chamber 40 adjacent the indication "BAD". However, when the pressure in the chambers is increased above the minimum test pressure, the buoyant force exerted upon the bead 42 exceeds the weight of the bead, and the bead floats upon the air within the indicator chamber 40, adjacent the indication "GOOD".

Figure 4:
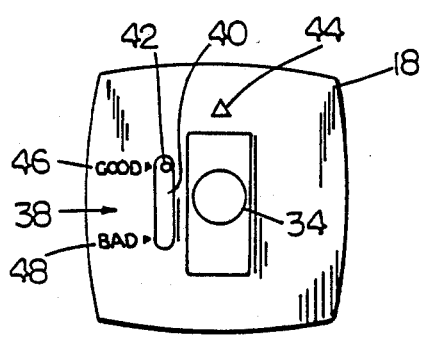
FIG. 4 is a plan view of the base surface of the device.
Figure 3:
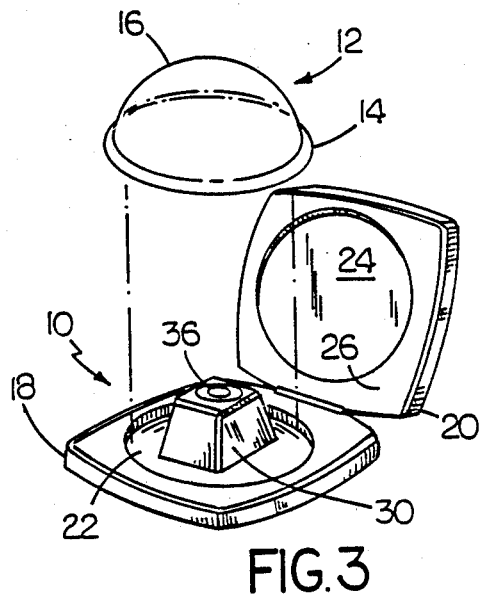
FIG. 3 is another perspective view of the device of the invention, shown with the cover open for receiving a vaginal diaphragm.
Figure 5:
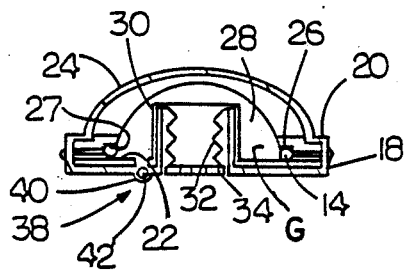
FIG. 5 is a side sectional view of the device containing a vaginal diaphragm.

To use the device 10 of the present invention, a vaginal diaphragm 12 is inserted and the cover 20 is firmly closed, clamping the ring 14 in place. Next, the device is held so that the arrow 44 points upward. At this time, the pressure within the pressure chamber 28 and the indicator chamber 40 is atmospheric, and the indicator bead 42 rests at the bottom of the chamber 40. This condition is shown in FIG. 2. Next, the button 34 is repeatedly depressed, increasing the pressure within the chambers 28 and 40. When the pressure has increased to the predetermined test pressure, e.g., approximately one p.s.i. above atmospheric, the buoyant force exerted on the bead 42 exceeds the weight of the bead causing it to rise within the indicator chamber 40 to a position next to the word "good" 46. This condition is shown in FIG. 4. The final step in testing the diaphragm is to observe the position of the indicator bead 42 for a period of time, preferably on the order of 15 seconds. If the indicator bead remains at the top of the indicator chamber 40, then the integrity of the vaginal diaphragm is assured and the diaphragm has passed the test and may be used. If, however, the indicator bead 42 falls within the chamber 40 toward the "bad" 48 position, the test indicates that an unacceptable level of porosity exists in the diaphragm and that it should not be used.

Figure 6:
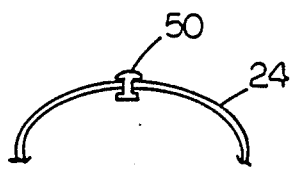
FIG. 6 is a partial side sectional view, showing an alternate embodiment.

Of course, loss of pressure within the pressure chamber 28 can be indicated by other means. For example, the cover 24 may be sized and configured to cooperate with the expansion of the diaphragm when pressurized, so that an increase in pressure of approximately one p.s.i. would cause the membrane 16 to come into non-sealing engagement with an indicator in the cover, e.g., a protruding button 50, as shown in FIG. 6. When the diaphragm is inflated, the protruding button is 50 is driven outward, and could expose indicia such as the word "good". In such an embodiment, the indicator may be observed for a period of time, such as 15 seconds, and if the membrane has an excess of porosity, the diaphragm will deflate and disengage from the indicator, the button 50 falling back into the cover 24.

Engineering tests have been performed which indicate that a 0.030 inch pin puncture causes a noticeable pressure drop in less than 15 seconds from an initial overpressure of one p.s.i. above atmospheric.

Other embodiments are within the following claims.

I claim:

1. A device for testing the integrity of a vaginal diaphragm having an annular ring about a membrane desired to be nonporous, comprising:
   a base member defining a surface for engaging said ring in sealing relationship and further adapted to define, with said membrane, a pressure chamber,
   clamping means for clamping said ring in sealing relationship upon said surface,
   pressurizing means for creating an inflating pressure condition in said chamber of a level predetermined to cause loss of air from said chamber through said membrane if said membrane has in excess of a predetermined maximum degree of porosity,
   means of indicating loss of air from within said chamber, and
   a protective carrying case for said vaginal diaphragm, said base member forming a first element of said case, sized and constructed to receive said vaginal diaphragm, and said case further comprising a cover sized and constructed to be disposed upon said base member.

2. The device of claim 1 wherein said cover defines said clamp means.

3. The device of claim 2 wherein said cover when closed upon said base is constructed and arranged to accommodate expansion of said vaginal diaphragm in response to said pressure condition.

4. The device of claim 2 wherein said cover is hingedly attached to said base member, and said ring, with said cover closed upon said base member, is held by said clamp means defined by said cover in sealing relationship upon said surface defined by said base member.

5. The device of claim 1 wherein said pressurizing means comprises a bellows and a one way valve for flow of air into said chamber.

6. The device of claim 1 wherein said indicating means comprises an indicating chamber in fluid communication with said pressure chamber, and a pressure responsive element within said indicating chamber.

7. The device of claim 1 wherein said indicating means comprises said cover sized and configured to cooperate with said diaphragm to indicate loss of air from said chamber.

8. The device of claim 1 wherein said indicating means comprises a pressure responsive element in said cover.

9. An assembly for transporting and integrity-testing of a vaginal diaphragm comprising,
   a protective carrying case, and,
   disposed therewithin, a vaginal diaphragm having an annular ring about a membrane desired to be nonporous,
   said case comprising:
      a base member defining a surface adapted to engage said ring in sealing relationship, said vaginal diaphragm disposed upon said surface, said base member and said membrane together adapted to define a pressure chamber,
      a cover sized and constructed to be disposed upon said base, with said vaginal diaphragm within said container, said cover defining clamping means for urging said ring into sealing engagement upon said surface,
   pressurizing means for creating an inflating pressure condition within said chamber of a level predetermined to cause loss of air from said chamber through said membrane if said membrane has in excess of a predetermined maximum degree of porosity, and
   means for indicating loss of air from within said chamber.

10. The assembly of claim 9 in the form of a prepackaged unit suitable for distribution or sale.

11. The assembly of claim 9 wherein said cover is constructed and arranged to accommodate expansion of said vaginal diaphragm to said pressure condition within said protective carrying case.

12. The assembly of claim 9 wherein said cover is hingedly attached to said base member, and said ring, with said cover closed upon said base member, is held by said clamp means defined by said cover in sealing relationship upon said surface defined by said base member.

* * * * *